United States Patent
Grosse et al.

(10) Patent No.: US 8,642,539 B2
(45) Date of Patent: Feb. 4, 2014

(54) METHOD FOR TREATING A DISEASE CHARACTERIZED BY REDUCED APPETITE

(75) Inventors: Johannes Grosse, Cambridge (GB); Helen Heffron, Cambridge (GB); Kate Day, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 399 days.

(21) Appl. No.: 12/675,724

(22) PCT Filed: Sep. 5, 2008

(86) PCT No.: PCT/GB2008/003023
§ 371 (c)(1),
(2), (4) Date: May 5, 2010

(87) PCT Pub. No.: WO2009/030931
PCT Pub. Date: Mar. 12, 2009

(65) Prior Publication Data
US 2010/0272727 A1   Oct. 28, 2010

(30) Foreign Application Priority Data
Sep. 7, 2007 (GB) .................................. 0717450.1

(51) Int. Cl.
*A61K 38/28* (2006.01)
*A61K 38/16* (2006.01)
(52) U.S. Cl.
USPC .......................................... 514/4.8; 514/12.7
(58) Field of Classification Search
None
See application file for complete search history.

(56) References Cited

U.S. PATENT DOCUMENTS 7,638,490 B2 * 12/2009 Hida et al. ..................... 514/1.1
2008/0269118 A1 * 10/2008 Aparicio et al. ................ 514/12

FOREIGN PATENT DOCUMENTS

| EP | 1 721 971 A1 | 11/2006 |
| WO | WO 2005/014616 A3 | 2/2005 |
| WO | WO 2005/124361 A3 | 12/2005 |

OTHER PUBLICATIONS

Chen, J. et al. "Pharmacological Characterization of Relaxin-3/INSL7 Receptors GPCR135 and GPCR142 from Different Mammalian Species" *The Journal of Pharmacology and Experimental Therapeutics*, Jan. 2005, 312(1):83-95.
Conklin, D. et al. "Identification if INSL5, a New Member of the Insulin Superfamily" *Genomics*, 1999, 60:50-56.
Halls, M.L. et al. "Relaxin Family Peptide Receptors—former orphans reunite with their parent ligands to activate multiple signalling pathways" *British Journal of Pharmacology*, 2007, 150:677-691.
Kuei, C. et al. "R3(BΔ23—27)R/I5 Chimeric Peptide, a Selective Antagonist for GPCR135 and GPCR142 over Relaxin Receptor LGR7: In Vitro and In Vivo Characterization" *The Journal of Biological Chemistry*, Aug. 31, 2007, 282(35):25425-25435.
Liu, C. et al. "Identification of Relaxin-3/INSL7 as a Ligand for GPCR142" *The Journal of Biological Chemistry*, Dec. 12, 2003, 278(50):50765-50770.
Liu, C. et al. "INSL5 is a High Affinity Specific Agonist for GPCR142 (GPR100)" *The Journal of Biological Chemistry*, Jan. 7, 2005, 280(1):292-300.
Liu, C. et al. "Relaxin-3, INSL5, and Their Receptors" *Results and Problems in Cell Differentiation*, 2008, 46:213-237.
Van Der Westhuizen, E.T. et al. "Relaxin family peptide receptors—from orphans to therapeutic targets" *Drug Discovery Today*, Aug. 2008, 13(15-16):640-651.
Zhu, J. et al. "Identification of the domains in RXFP4 (GPCR142) responsible for the high affinity binding and agonistic activity of INSL5 at RXFP4 compared to RXFP3 (GPCR135)" *European Journal of Pharmacology*, Aug. 2008, 590:43-52.
Asakawa, A et al., "Antagonism of ghrelin receptor reduces food intake and body weight gain in mice" *Gut*, 2003, 52:947-952.

* cited by examiner

*Primary Examiner* — Christine J Saoud
(74) *Attorney, Agent, or Firm* — Saliwanchik, Lloyd & Eisenschenk

(57) ABSTRACT

Insl5 has been found to be orexigenic, i.e. it increases appetite. Insl5, or a derivative or fragment thereof that retains the ability to bind to the GPR100 receptor, or an Insl5 antibody, are useful in therapy, in particular to treat anorexia nervosa, bulimia, cachexia or wasting disease.

4 Claims, 10 Drawing Sheets

METHOD FOR TREATING A DISEASE CHARACTERIZED BY REDUCED APPETITE

CROSS-REFERENCE TO RELATED APPLICATION

This application is the U.S. national stage application of International Patent Application No. PCT/GB2008/003023, filed Sep. 5, 2008, the disclosure of which is hereby incorporated by reference in its entirety, including all figures, tables and amino acid and nucleic acid sequences.

FIELD OF THE INVENTION

This invention relates to a medicament useful in controlling appetite and therefore useful in treating diseases characterised by altered appetite, the medicament is also useful in treating certain colonic disorders.

BACKGROUND TO THE INVENTION

Maintaining a healthy body weight has both medical and cosmetic benefits and there is a large industry devoted to gaining or losing weight. Eating disorders are recognised as an increasing epidemic, with both excessive and insufficient food intake increasing in occurrence. Common eating disorders are overeating (leading to obesity), anorexia nervosa and bulimia. Cachexia, i.e. the unintentional loss of weight, is also a major problem in certain diseases.

Nearly two thirds of the adult population of the USA is overweight or obese, based on a body mass index (BMI, i.e. body weight in kilogram divided by the squared height in m) above 25 or 30, respectively. The obese subgroup has increased from 13.3% in 1964 to more than double that value with 32.9% in 2004 (Ogden et al, Gastroenterology 132, 2087-102 (2007) and Bray, G. A. & Bellanger, T. Endocrine 29, 109-17 (2006)).

Anorexia nervosa is characterised by low body weight and body image distortion, with an excessive fear of gaining weight. It has a prevalence of 0.3% to 1.3% in the Western population; this incidence is thought to be rising (Bulik et al, Int J Eat Disord 2005; 37:S2-S9).

Bulimia (also known as bulimia nervosa) is characterized by binge-eating followed by intentional purging, such as vomiting. It has a prevalence of approximately 1% in the Western adult population, although prevalence is significantly higher in young women (Bushnell et al, Psychol Med. 1990 August; 20(3): 671-680).

Cachexia involves muscle atrophy, a loss of weight and a loss of appetite in a subject that is not actively trying to lose weight. Cachexia is often seen in late-stage cancer and AIDS patients.

The exact mechanisms involved in gaining, losing or maintaining body weight are not understood. It is known that eating disorders and cachexia are governed by a combination of psychological and physiological factors. It is known that gastrointestinal hormones are involved in the regulation of appetite.

In particular, the hormone leptin is known to be a fat-derived anorexigenic hormone that signals the fuel storage level to the brain (Zhang, Y. et al. Nature 372, 425-32 (1994)). In short, leptin reduces appetite. Several other gastrointestinal anorexigenic hormones have been identified (Drucker, D. J. J Clin Invest 117, 24-32 (2007)).

Conversely, the gastrointestinal hormone ghrelin is the only known orexigenic hormone, i.e. the only hormone that is known to increase appetite (Asakawa, A. et al. Gut 52, 947-52 (2003)). In contrast to anorexigenic hormones which are secreted in response to food intake, ghrelin surges before meal initiation and is suppressed by food intake. Administration of ghrelin stimulates food intake in a wide variety of species.

The identification of receptors for hormones that affect appetite and food intake has been the subject of considerable scientific research in recent years. Recently, the G-protein coupled receptor GPR100 (also referred to as GPCR 142, relaxin-3 receptor-2 and RXFP4) was identified as involved in the regulation of obesity (WO-A-2005/124361). The peptide hormone Insl5 has recently been identified as the endogenous ligand of GPR100 (Liu at al J. Biol. Chem., Vol. 280, Issue 1, 292-300, Jan. 7, 2005).

Although a number of hormones, such as leptin and ghrelin, have been identified as potential therapeutics to regulate body weight, clinical results to date (for leptin at least) have been disappointing. Therefore, there remains a strong need to identify further agents that can regulate appetite and food intake.

SUMMARY OF THE INVENTION

The present invention is based on the surprising realisation that the Insl5 peptide is orexigenic, i.e. it increases appetite.

According to a first aspect of the invention, Insl5, or a derivative or fragment thereof that retains the ability to bind to the GPR100 G-protein coupled receptor, or an Insl5 antibody, is used in therapy.

According to a second aspect of the invention, Insl5 or a derivative or fragment thereof that retains the ability to bind the GPR100 G-protein coupled receptor is used in the manufacture of a medicament for the treatment of IBS, constipation or diarrhoea.

According to a third aspect of the invention, Insl5 or a derivative or fragment thereof that retains the ability to bind the GPR100 G-protein coupled receptor is used in the manufacture of a medicament for the treatment of a disease characterised by reduced appetite.

According to a fourth aspect of the invention, an Insl5 antibody is used in the manufacture of a medicament for the treatment of a disease characterised by increased appetite.

According to a fifth aspect of the invention, a composition comprises Ghrelin, or a derivative or fragment thereof that retains the ability to bind hGHSR1a, and Insl5, or a derivative or fragment thereof that retains the ability to bind the GPR100 G-protein coupled receptor.

According to a sixth aspect of the invention, a composition comprises a Ghrelin antibody and an Insl5 antibody.

According to a seventh aspect of the invention, a vaccine comprises Insl5 or an immunogenic derivative or fragment thereof.

According to an eighth aspect of the invention, a vaccine comprises a composition according to the fifth aspect.

According to a ninth aspect of the invention, Insl5 or a derivative or fragment thereof that retains the ability to bind the GPR100 G-protein coupled receptor, or an Insl5 antibody, is used cosmetically to alter food intake and therefore alter the weight of a subject.

BRIEF DESCRIPTION OF THE FIGURES

The invention is described with reference to the following figures, wherein.

DETAILED DESCRIPTION OF THE INVENTION

Figure 1:
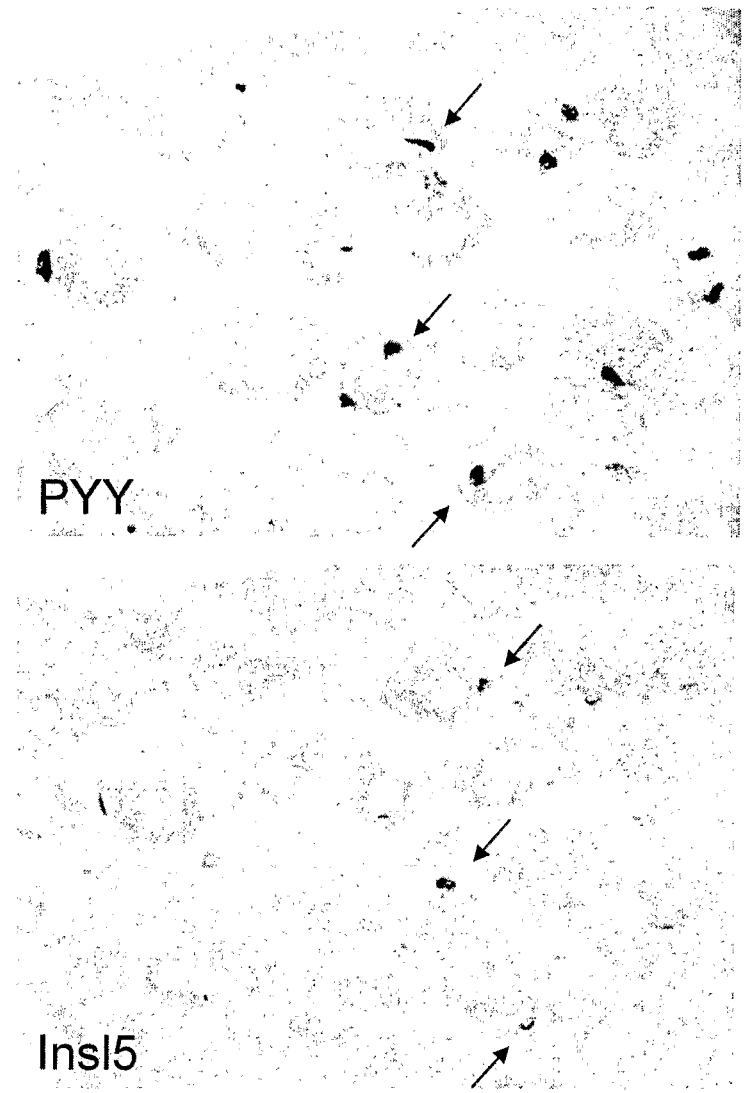
FIG. 1 demonstrates the expression of Insl5 in enteroendocrine cells of the colon.

The present invention is based on the realisation that Insl5 is orexigenic and therefore altering the amount of Insl5 present in a subject allows the appetite of the subject to be controlled. This is useful in treating diseases where appetite is altered. Furthermore, it has been found that Insl5 increases the propulsion of nutrients in the gastrointestinal (GI) tract and a drop in Insl5 upon feeding initiation is involved in the GI reflex. Given these effects on colonic motility, Insl5 is useful in treating diseases/disorders involving colonic motility alterations such as diarrhoea, predominant irritable bowel syndrome and functional diarrhoea.

Diseases characterised by altered appetite are commonly referred to as eating disorders. As used herein, the term "eating disorders" includes diseases characterised by both an increase in appetite, such as obesity, and a decrease in appetite, such as anorexia nervosa, bulimia, cachexia and wasting syndromes. As Insl5 has been found to additionally have an effect on colonic motility it is useful in treating conditions linked to altered colonic motility. Examples of such diseases include constipation, irritable bowel syndrome (IBS), diarrhoea and diarrhoea-IBS.

For the avoidance of doubt, Insl5, or a derivative or fragment thereof that retains the ability to bind the GPR100 G-protein coupled receptor, or an Insl5 antibody, can be used in therapy. Preferably, the therapy is treatment of a disease characterised by altered appetite or altered colonic motility.

The data presented in the examples indicate that Insl5 acts through GPR100 and induces a significant increase in food intake in mice over saline injected control animals. Therefore, controlling the level of Insl5 will control food intake.

As used herein, the term "Insl5" refers to insulin-like peptide 5. This peptide is known in the art as a 135 amino acid precursor (Swiss Prot accession number Q9Y5Q6) that is processed by cleavage resulting in a 45 amino acid residue mature peptide comprising an "A" chain and a "B" chain connected by disulfide bonds. The sequence of the precursor and the mature peptide is disclosed in FIG. 1 panels A and B of Liu et al, J. Biol. Chem, 280, issue 1, 292-300, Jan. 7, 2005.

The precursor or the mature peptide can be used in accordance with the current invention. Preferably, the mature peptide is used.

Derivatives of Insl5 are also within the scope of the invention. The skilled person will realise that amino acid residues in Insl5 can be altered or deleted without altering the function of Insl5. Derivatives of Insl5 that retain the biological function of Insl5 are therefore within the scope of the invention. As used herein, the biological function of Insl5 is the ability to increase appetite. A further biological function is the ability to bind to the GPR100 G-protein coupled receptor. This receptor is known in the art, for example as disclosed in WO-A-2005/124361, which is incorporated herein by reference. A derivative of Insl5 is within the scope of the invention if it binds to GPR100. More preferably, the derivative binds to GPR100 with a Kd in the nanomolar range, more preferably with a Kd of 100 nM or greater, for example 50 nM or greater, preferably 20 nM or greater, yet more preferably 10 nM or greater, for example 2.5 nM or greater. For the avoidance of doubt, a "greater" Kd refers to stronger binding, which is represented by a smaller Kd value.

Mature Insl5 displaces the relaxin-3 peptide from GPR100 with high affinity, in the nanomolar range. Preferred derivatives of Insl5 therefore also displace relaxin-3 with high affinity. Preferably, the Ki of the derivative is between 0.01 and 100 nM, preferably between 0.5 and 10 nM, for example 1.5 nM. The amino acid sequence for precursor Insl5 protein is shown as SEQ ID No. 1. The mature peptide A chain and B chain are shown as SEQ ID Nos. 2 and 3, respectively. Homologues within the scope of the invention will typically have greater than 70% sequence identity to SEQ ID No. 1 or SEQ ID Nos. 2 and 3. More preferably, homologues will have greater than 80% sequence identity, e.g. 85%, 90%, 95%, 96%, 97%, 98% and 99% sequence identity.

Sequence identity with respect to the sequences presented herein can be determined by a simple "eyeball" comparison (i.e. a strict comparison) of any one or more of the sequences with another sequence to see if that other sequence has, for example, at least 70% sequence identity to the sequence(s).

Relative sequence identity can also be determined by commercially available computer programs that can calculate % identity between two or more sequences using any suitable algorithm for determining identity, using for example default parameters.

A typical example of such a computer program is CLUSTAL. Other computer program methods to determine identify and similarity between the two sequences include but are not limited to the GCG program package (Devereux et al 1984 Nucleic Acids Research 12: 387) and FASTA (Atschul et al 1990 J Molec Biol 403-410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (Ausubel et al., 1999 ibid-Chapter 18), FASTA (Atschul et al., 1990, J. Mol. Biol., 403-410) and the GENEWORKS suite of comparison tools. Both BLAST and FASTA are available for offline and online searching (Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance.

An example of such a matrix commonly used is the BLOSUM52 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail at http://www.ncbi.nih.govBLAST/blast help.html, which is incorporated herein by reference. The search parameters can also be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Scz. USA* 90:5873-7; see http://www.ncbi.nih.govBLAST/blast help.html) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at http://www.ncbi.nlm.nih.gov perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions.

(See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM 120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short periodicity internal repeats, as determined by the XNU program of Clayerie & States (1993) Computers and Chemistry 17:191-201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g. "NNNNNNNNNNNNN") and the letter "X" in the protein sequences (e.g. "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at http://www.ncbi.nlm.nih.govBLAST. In some embodiments, no gap penalties are used when determining sequence identity.

The skilled person will realise that chemical stabilisation of Insl5 is possible. Chemically stabilised Insl5 is therefore within the scope of the term "derivative". A preferred stabilised Insl5 is pegylated Insl5. Fragments of Insl5 that retain the biological function of mature Insl5 are within the scope of the invention. The fragment can be any length that retains the function of mature Insl5, i.e. the ability to increase appetite and bind the GPR100 G-protein coupled receptor. Preferably, the fragment is at least 20 amino acid residues long, more preferably at least 25 residues, for example 30, 35 or 40 residues or more.

As used herein, the term "Insl5" includes derivatives and fragments thereof and refers to Insl5 from any species. Preferably, the Insl5 is mammalian, more preferably human.

It should be noted that, although the discussion herein focuses on Insl5 peptides, the use of a polynucleotide, such as DNA or RNA, that codes for an Insl5 peptide, derivative or fragment thereof, is within the scope of the invention.

A number of products and compositions comprising Insl5 are disclosed herein. As the aim of the invention is to administer these products and compositions to a patient, it is preferred that they are formulated in combination with at least one pharmaceutical excipient or diluent.

It has been found that Insl5 is orexigenic. The term "orexigenic" is well known in the art as defining the ability of a compound to increase appetite. Therefore, Insl5 can be used to increase appetite, and therefore increase food intake, to treat diseases characterised by reduced appetite. Examples of diseases characterised by reduced appetite are anorexia nervosa, bulimia and cachexia, in particular tumour and tumour-treatment associated cachexia. Administering Insl5 to a subject suffering from one or more of these diseases will increase the subject's appetite and therefore increase the food intake of the subject, treating the disease.

Insl5 (or a derivative thereof) can also be administered to patients suffering from a disorder associated with alterations in colonic motility. Such disorders include constipation, diarrhoea and irritable bowel syndrome. Administering Insl5 to a patient suffering one or more of the disorders will increase the propulsion of nutrients in the GI tract, helping to remove blocked nutrients or nutrients infected by unwanted bacteria or other contaminants.

In an alternative aspect of the invention, Insl5 antibodies can be used to treat diseases characterised by increased appetite. Insl5 itself increases appetite. Therefore, an antibody to Insl5 will reduce the amount of circulating Insl5 and therefore reduce appetite. Administering an Insl5 antibody to a subject suffering from a disease characterised by increased appetite will therefore reduce their appetite and reduce the intake of food by the subject. A preferred disease characterised by increased appetite is obesity. Obesity is a feature of the metabolic syndrome and other factors of the metabolic syndrome can therefore also be treated using Insl5 antibodies, such as type 2 diabetes and dyslipidemia.

To treat a disease characterised by increased appetite, an Insl5 antibody can be administered to a person suffering from the disease. As used herein, the term "Insl5 antibody" refers to an immunoglobulin molecule that binds, preferably specifically, to Insl5.

As used herein, the term "antibody" refers to an immunoglobulin-based molecule that binds to an antigen. The term "antibody" encompasses all five classes of immunoglobulins (IgG, IgE, IgA, IgM and IgD). Antibody fragments and variations such as Fab and scFV fragments are within the scope of the invention. The skilled person will realise that when an antibody fragment is intended for use in passive immunisation, the Fc region in preferably present. A monoclonal antibody that binds to Insl5 or a derivative or fragment thereof is within the scope of the invention; the use of Insl5 to create monoclonal antibodies is also within the scope of the invention. Humanised antibodies are a preferred embodiment.

Administering an antibody, to a specific antigen, to a subject is known in the art as "passive immunisation". Preferably, the antibody is administered in conjunction with at least one pharmaceutically-acceptable excipient.

As an alternative to administering an Insl5 antibody to a person suffering from a disease characterised by increased appetite, the subject can be administered with a vaccine comprising Insl5. This vaccine will result in "active immunisation" against Insl5. Preferably, one or more fragments or derivatives of Insl5 are used as a vaccine. In this embodiment, the fragment or derivative does not need to retain the biological function of Insl5. However, a fragment or derivative used in a vaccine must retain the ability to elicit an immunogenic response, i.e. it must be an "immunogenic" fragment or derivative. Preferably, the immunogenic response generated by the fragment or derivative is similar to the response generated by the mature Insl5 peptide. An antibody that binds to such a fragment or derivative will also bind to the mature Insl5 peptide (in the region that corresponds to the fragment or derivative). Preferably, antibodies raised in an immunogenic response against a fragment or derivative will bind specifically to the mature Insl5 peptide. As used herein, reference to "specific binding" refers to an antibody binding selectively to a specific antigen or epitope and not to other (non-related) antigens or epitopes. Preferably, the binding affinity between an Insl5 fragment or derivative and an antibody is in the micromolar range, for example 50 µM or less, more preferably 10 µM or less.

The preparation of vaccines incorporating Insl5 will be straightforward to those skilled in the art. Vaccine compositions can be formulated with suitable pharmaceutically-acceptable carriers or adjuvants, e.g. alum, as necessary or desired, to provide effective immunisation against infection. Suitable adjuvants include, but are not limited to, aluminium salts, squalene mixtures, aquiline mixtures, saponin derivatives, immunostimulating complexes (ISCONs), non-ionic block copolymer surfactants and β-glucan.

It is well known that a number of diseases characterised by altered appetite are medical conditions. However, the skilled person will also recognise that controlling the weight of a subject has a cosmetic application. Therefore, in one embodiment of the invention, Insl5 or an Insl5 antibody is used in a cosmetic method to cause a subject to gain or lose weight. As used herein, the term "cosmetic" is to be given its usual meaning in the art, i.e. relating solely to altering, preferably improving, the appearance of a person without a significant medical benefit.

The invention is based on the surprising realisation that Insl5 is an orexigenic hormone. Only one other orexigenic hormone, Ghrelin, is known. According to one aspect of the invention, a composition comprises Ghrelin or a derivative or fragment thereof and Insl5 or a derivative or fragment thereof.

Ghrelin obtained from any species can be used. Human Ghrelin is preferred; this is well-known in the art as a 28-amino acid mature peptide that is a potent agonist at the human growth hormone secretagogue receptor 1A (hGHSR1a). Acylation of residue 3 of Ghrelin by an n-octanoyl acid is essential for Ghrelin's activity. The sequence of human Ghrelin is known in the art, with Swiss Prot accession no. Q9UBU3 (117 amino acid residue precursor, of which the mature 28 residue peptide is residues 24 to 51). The precursor or the mature Ghrelin peptide can be used in accordance with the correct invention. Preferably, the mature peptide is used. Derivatives and fragments of Ghrelin that maintain the ability to agonise hGHSR1a are within the scope of the invention. It is known that short peptides encompassing the first 4 or 5 residues of Ghrelin retain the ability to activate functionally hGHSR1a. Specifically, the Gly-Ser-Ser(n-octanoyl)-Phe segment is the "active core" required for agonist potency and function (Bednarek et al, J. Med. Chem., 43(23), 4370-4376, 2000). As indicated above for Insl5, although the discussion of Ghrelin herein focuses on the peptide, the use of a polynucleotide such as RNA or DNA that codes for Ghrelin, or a fragment or derivative thereof, is within the scope of the invention.

Without wishing to be bound by theory, it is believed that the combination of Ghrelin and Insl5 is advantageous over the separate administration of these two hormones.

A vaccine comprising Insl5 or an immunogenic fragment or derivative thereof and Ghrelin or an immunogenic fragment or derivative thereof is within the scope of the invention.

A composition comprising a Ghrelin antibody and an Insl5 antibody is within the scope of the invention. As used herein, a Ghrelin antibody is an immunoglobulin molecule (as defined above) that binds, preferably specifically, to Ghrelin.

Again, without wishing to be bound by theory, it is believed that a combination of an Insl5 antibody and a Ghrelin antibody has a synergistic effect on reducing food intake. This combination is believed to be superior to alternative approaches such as administration of anorexigenic hormones. In particular, it has been observed that hunger, satiety and nausea are sensations on a continuum. Therefore, the therapeutic window of anorexigenic compounds is usually narrow. Inducing satiety is often difficult to separate from the nausea induced at slightly higher concentrations. This general limitation does not apply to the simultaneous inhibition of the two orexigenic hormones, Ghrelin and Insl5. To increase the efficacy even further, a combination of a Ghrelin antibody and an Insl5 antibody with a low dose anorexigenic substance (which does not induce nausea) is possible.

The invention is described with reference to the following non-limiting examples.

EXAMPLES

Abbreviations Used in the Examples
wt or +/+—wild type mice of 129/SvEv strain
GPR100-/-, -/- or GPR100 deficient:—animals with homozygous deletion of GPR100, 129/SvEv background
RER—respiratory exchange rate
EE—energy expenditure
HFD—high fat diet
HCD—high carbohydrate diet

Example 1

Insl5 is a Hormone Secreted from Enteroendocrine Cells of the Colon in Response to the Feeding Condition To explore the subtle metabolic phenotype observed in GPR100 deficient animals the expression pattern of GPR100 and its endogenous ligand Insl5 was investigated.

Expression data published for GPR100 suggest a broad distribution in peripheral tissues excluding the CNS. Most other tissue expression data are not consistent across publications. For example, Northern and dot blot data suggest highest expression in kidney, liver, skeletal muscle and heart but no expression in colon or small intestine whereas a quantitative rtPCR revealed highest expression in colon, little expression in the kidney and no expression in heart or skeletal muscle. Expression data (not shown) in mouse tissues measured by rtPCR revealed highest expression in thymus, stomach, small intestine, and lung.

Expression data for the ligand are more conclusive. All published EST sequences are derived from either mouse intestine or thymus. The normalized EST expression in small intestine is roughly twice as high as in thymus. Based on these suggestive data an immunohistochemistry was performed using a commercially available antibody (Phoenix Pharmaceuticals GmbH, Germany). INSL5 was detected in some scattered epithelial cells of colonic crypts suggestive of enteroendocrine cells. Co-localization of Insl5 with PYY and chromogranin (not shown) in some but not all cells corroborated this notion (FIG. 1).

FIG. 1—Immunohistochemistry demonstrates the expression of Insl5 in enteroendocrine cells of the colon. Consecutive sections are stained for PYY or Insl5, respectively. Co-localization in the same cell is indicated by arrows. Of note, there are several PYY positive cells which are not Insl5 positive. In other sections the reverse is true, Insl5 positive cells do not stain for PYY.

Tissues were perfusion fixed using 4% paraformaldehyde in PBS, dehydrated, paraffin embedded and sectioned using standard methods. Commercially available polyclonal rabbit antibodies (Phoenix Pharmaceuticals GmbH, Germany) are used and detected with secondary biotinylated antibodies and ABC kit (Vectastain).

As INSL5 is secreted by enteroendocrine cells, it was investigated whether its plasma levels are related to the feeding state of the animals. Wild-type animals on normal chow diet were fasted overnight and blood samples were taken before and at several time points after refeeding. Insl5 levels were measured using a RIA (Phoenix Pharmaceuticals GmbH, Germany). After overnight fasting Insl5 levels were high and dropped significantly after 15 min. 1 hr after the start of refeeding the INSL5 levels reached a peak and were low again at later time points. A second peak was observed during the following night. A similar pattern is observed for the GPR100 deficient mice, although the peaks are delayed (FIG. 2) Ghrelin is not substantially altered by GPR100 deletion.

The observed pattern of Insl5 secretion might be a superposition of circadian activity patterns and feeding behaviour. Therefore the Insl5 levels in mice feeding ad libitum without previous fasting were investigated. The lowest Insl5 levels are observed during the night (FIG. 3). Wild type animals have higher levels during the day with a peak in the afternoon. These peaks are phase shifted to later time points in GPR100 deficient animals. As mice are nocturnal animals with the main feeding phase during night time this pattern of Insl5 secretion is consistent with an orexigenic function of the hormone. In conjunction with this notion is the generally much higher Insl5 level in fasted animals during the refeeding period (5-10 pg/0.1 ml at most time points) as compared to the levels of animals fed ad libitum (~0.1-2 pg/0.1 ml). Interestingly, the highest levels are observed during the night of the refeeding period (FIG. 2).

Figure 2:
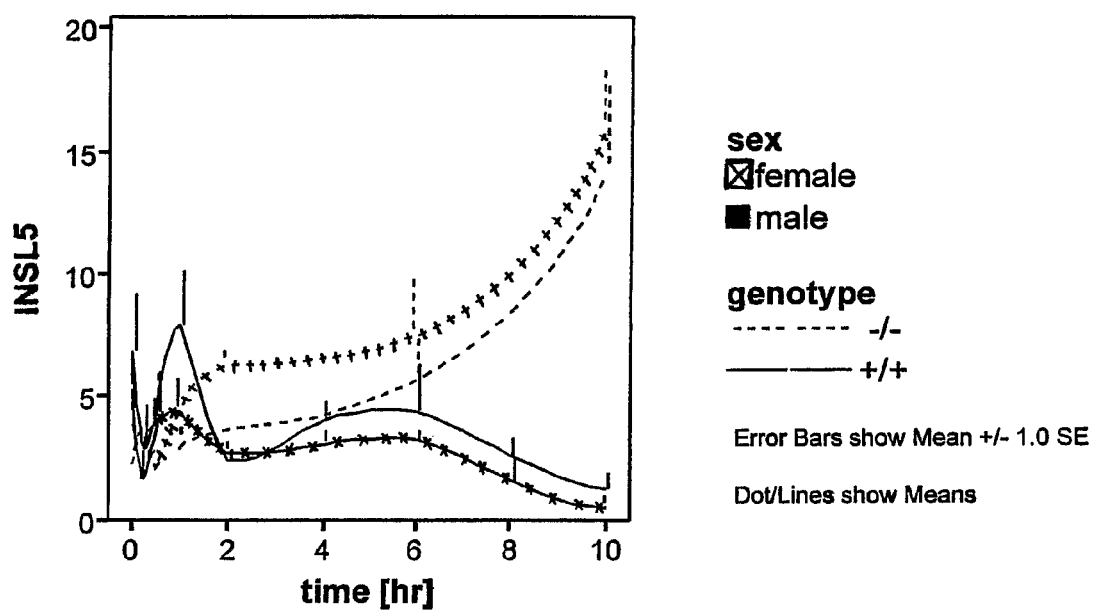
FIG. 2 demonstrates Insl5 levels in response to fasting and feeding.
Figure 3:
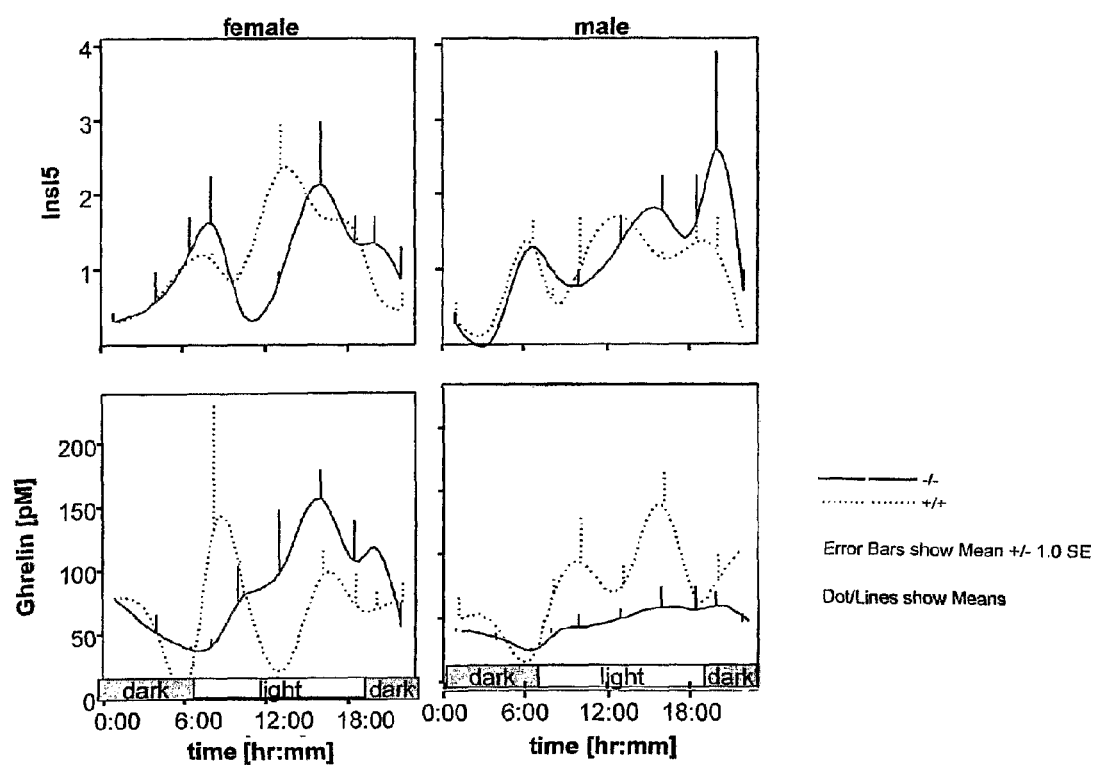
FIG. 3 illustrates the circadian rhythm of Insl5 levels.

FIG. 2—Insl5 levels in response to fasting and refeeding. Animals are fasted overnight. Refeeding starts at time point 0 and continues throughout the experiment. Samples are drawn before refeeding, 15 min, 30 min, 1 hr, 2, 4, 6, 8, hrs after refeeding. Some sampling times are omitted for the GPR100-/- mice. Because of the sample volume required the animals are killed at the sampling. 2 animals per sex, genotype and time point are used. The interpolating line is a $3^{rd}$ order LaGrange function.

The Insl5 levels of the fasted male and female wild-type animals starts at around 5 pg/0.1 ml. 15 min after refeeding there is a sharp drop. The levels increase again at 30 min to reach roughly the starting values at around 1 hr. At 2 hrs the levels are lower and decrease further for the remaining observation period.

FIG. 3—Circadian rhythm of Insl5 levels. The Insl5 nadir occurs during midnight, i.e. directly after the main feeding period of the animals. The peaks are delayed in the GPR100-/- mice and are realigned during night time. Similar phase shifts are observed in female KO mice for Ghrelin. In male KO mice there are no discernible peaks. Insl5 levels are generally lower in comparison to FIG. 2 (note the different ordinate scale for Insl5). The animals are killed at the sampling. 2 animals per sex, genotype and time point are used. The interpolating line is a $3^{rd}$ order LaGrange function.

These data suggest that the motivation to feed is mediated at least in part by Insl5.

Example 2

Alteration of Meal Size and Frequency and Macronutrient Preference in GPR100 Deficient Animals To explore further the loss of GPR100 on metabolism and feeding behaviour, 4 wt and 4 GPR100-deficient age-matched male mice were subjected to a fasting and refeeding procedure using a comprehensive laboratory animal monitoring system (CLAMS; Columbus Instruments Ltd.). The CLAMS is equipped with 8 chambers, per chamber two food hoppers monitoring the consumption of two diets independently, an infrared beam break based activity monitor, water intake monitoring, and an indirect calorimeter. The mice were offered a choice of a high fat diet (HFD; 35 kcal % carbohydrates, 45 kcal % fat) and a nearly iso-caloric high carbohydrate diet (HCD; 70 kcal % carbohydrates, 10 kcal % fat). After acclimatisation on day1 the animals were fasted overnight and back on the food choice from day2 to the end of the experiment 48 hrs later (FIG. 4).

Figure 4:
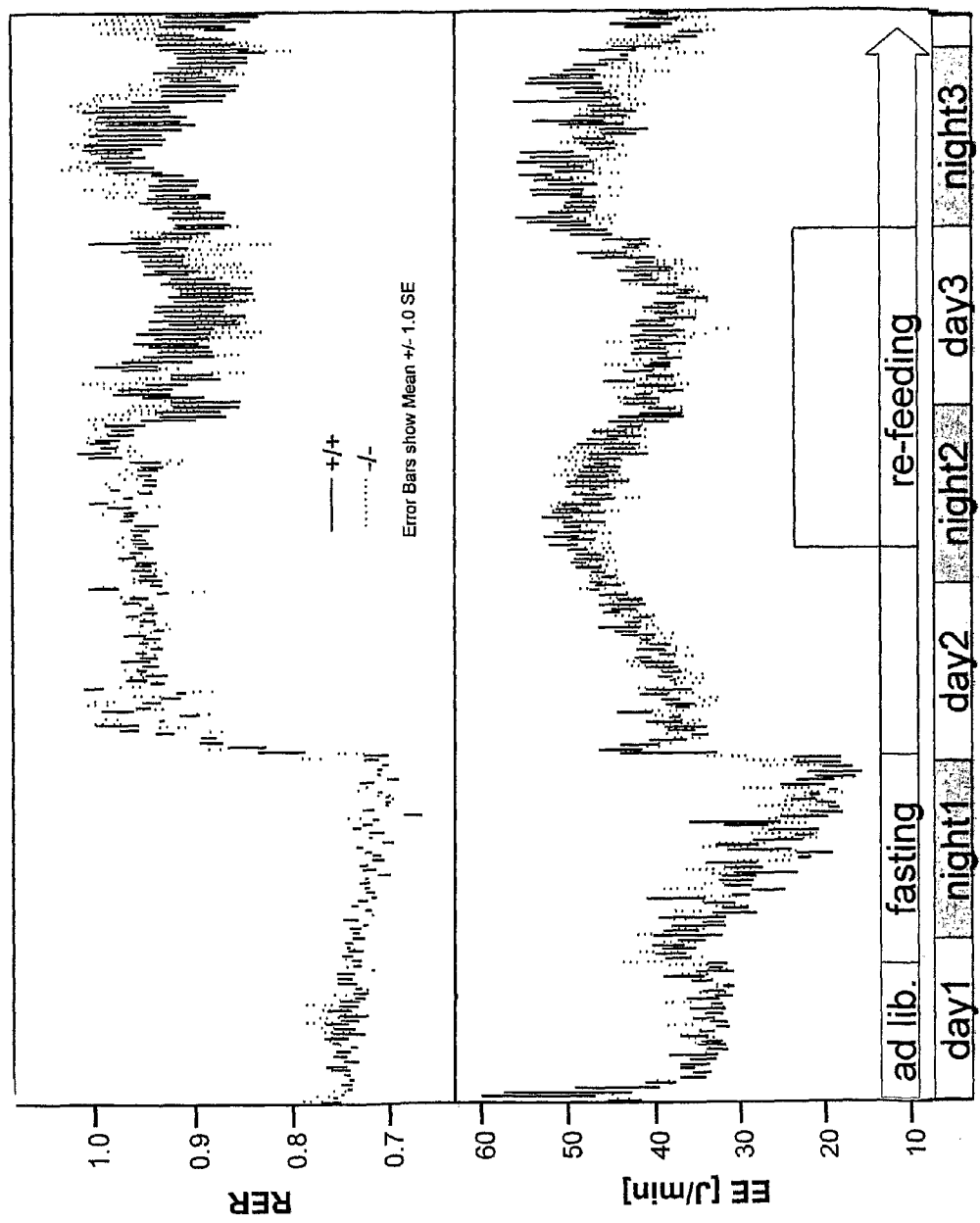
FIG. 4 illustrates the energy expenditure and respiratory exchange rate of 4 wild type and 4 GPR100 deficient mice in a comprehensive laboratory animal monitoring system.

FIG. 4—EE and RER in the CLAMS. 4 wt and 4 GPR100 deficient age matched male mice are subjected to a fasting and refeeding procedure using a comprehensive laboratory animal monitoring system (CLAMS; Columbus Instruments Ltd.).

During the fasting period the energy expenditure (EE) is declining to save energy, and the respiratory exchange ratio (RER, carbondioxyde produced per oxygen consumed) approaches 0.7 indicating that they rely on fat as fuel. After food is made available again on the morning of day1 the RER increases dramatically. An RER of 1 indicates that the animals burn exclusively carbohydrates. The natural rhythm of the RER is only re-established during day3 when the carbohydrate and fat stores have been refilled. The loose correlation of EE with RER observed during the remaining experiment reflects the normal alternation between fasting periods characterized by lower EE and RER and feeding periods (higher EE and RER). Accordingly, day2 and night2 are considered as refeeding period, day3 is a transition period and night3 represents the normal situation for an ad libitum fed animal.

The RER during night3 tends to be higher in the GPR100 deficient animals than in the wt. Due to the broad spectrum of RER distribution during that period the data are re-analyzed in the cumulative frequency plot (FIG. 5).

Figure 5:
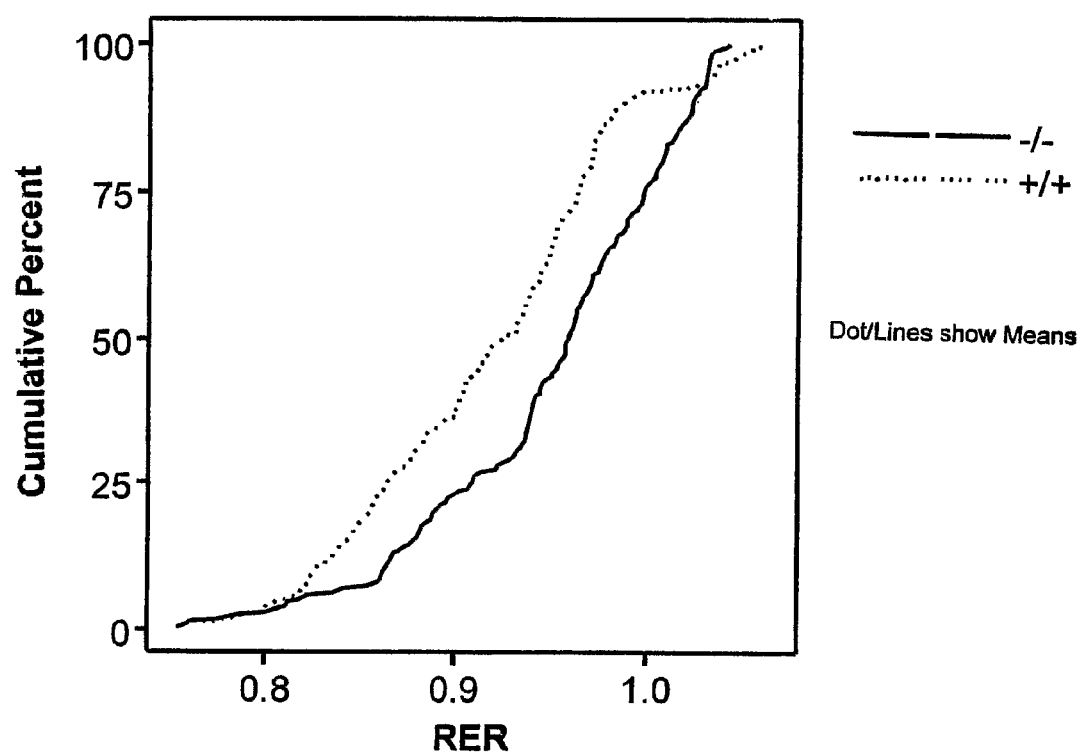
FIG. 5 shows the cumulative frequency analysis of the data shown in FIG. 4.

FIG. 5—Cumulative frequency analysis of the RER of wt and GPR100-/- mice from night3 of the experiment outlined in FIG. 4.

To investigate the cause for the different RER, the food consumption was analysed. Total cumulative food consumption is not different for the whole experiment (data not shown), and there is no difference with regard to the two diets during the refeeding period (day2-night2). After the refeeding period at day3 and night3 a significant difference develops. The GPR100-/- animals prefer the high carbohydrate diet as compared to the wt. The wt animals consequently consume more of the HFD (FIG. 6).

Figure 6:
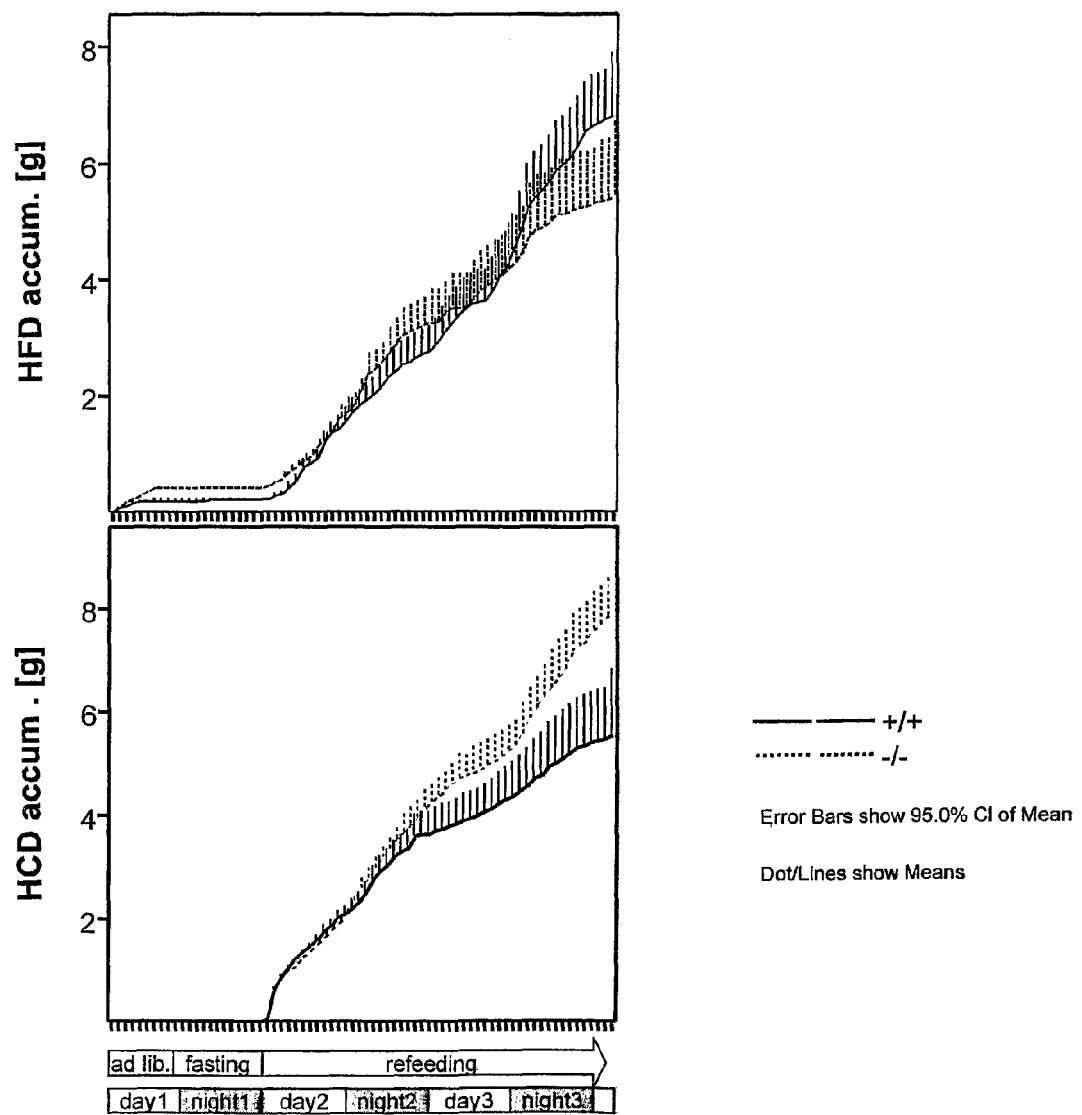
FIG. 6 illustrates the cumulative intake of the high fat diet and the high carbohydrate diet of the experiment outlined in FIG. 4.

FIG. 6-*Cumulative* intake of the high fat diet (HFD) and the high carbohydrate diet (HCD) of the experiment outlined in FIG. 4. Data are presented as means+95% confidence interval.

As there are no alterations of EE or activity patterns the difference in food preference is most probably the sole explanation for the elevated RER in the GPR100-/- mice. It is not uncommon for gastrointestinal hormones to affect food preferences besides other behavioural characteristics. Usually some macronutrients are more effective than others in inducing the secretion of a specific hormone. Conversely, Ghrelin has been shown to induce a preference for fat ingestion. This is inline with the observed preference for carbohydrates in GPR100-deficient animals. In reverse this implicates that Insl5 similar to Ghrelin increases fat consumption.

Figure 7:
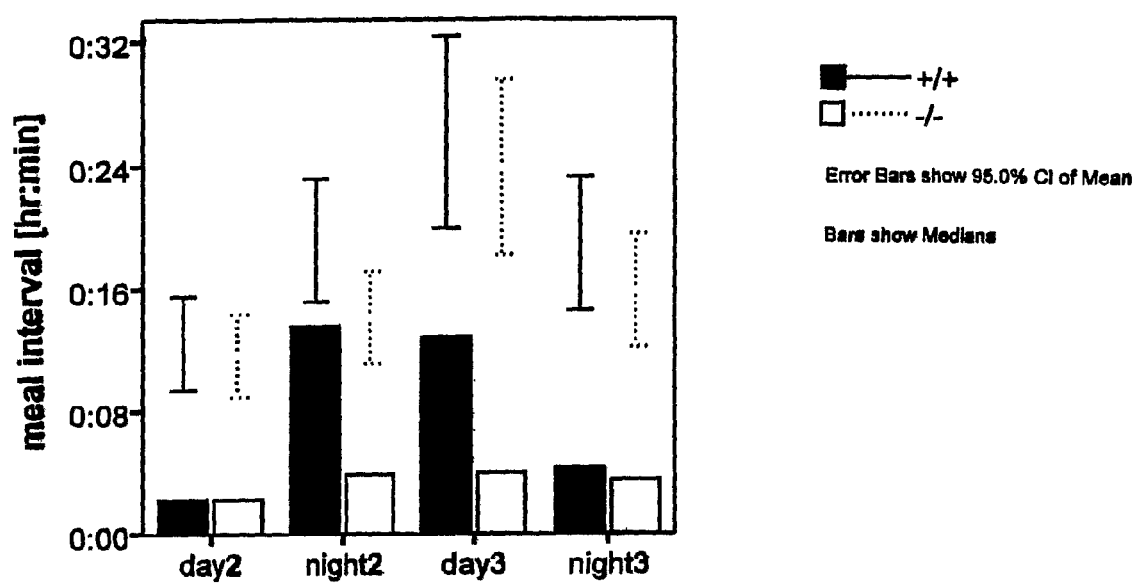
FIG. 7 illustrates the shorter (compared to wild type mice) meal intervals of GPR100 deficient mice during the refeeding period of the experiment outlined in FIG. 4.
Figure 8:
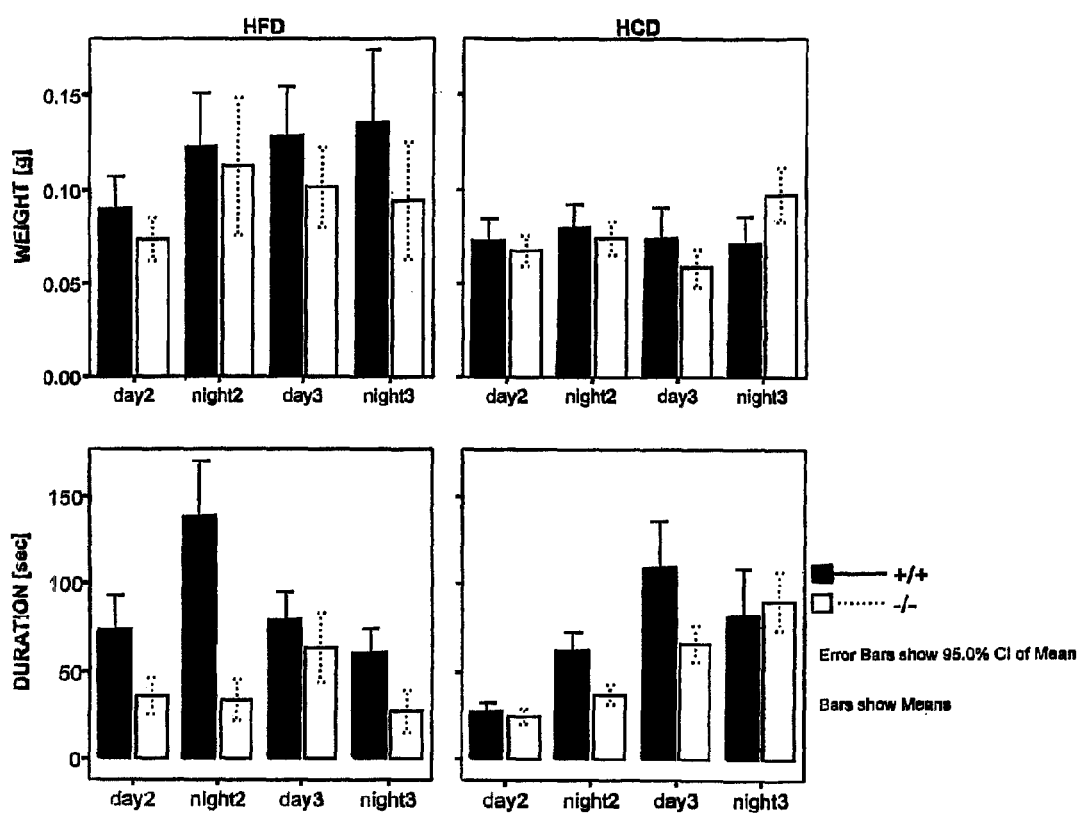
FIG. 8 illustrates a lower (compared to wild type mice) meal weight and shorter meal duration of GPR100 deficient mice during the refeeding period of the experiment outlined in FIG. 4.

Beyond the cumulative food intake, the pattern of individual meals was interesting. The meal intervals are not significantly different. During the refeeding period, especially night2 and day3, there is a trend for shorter meal intervals in the GPR100-/- mice (p=0.151; FIG. 7). In contrast, meal weight is significantly lower in GPR100-/- mice (p=0.002). Similarly, the duration of individual meals is significantly shorter (p=0.0001; FIG. 8). These findings suggest that GPR100 mediated Insl5 signals contribute to the motivation to feed and as previously shown in FIG. 6, Insl5 induces a preference for a high fat diet.

Example 3

Insl5 Administration Induces Feeding in Wt but not GPR100-/- Mice

Figure 9:
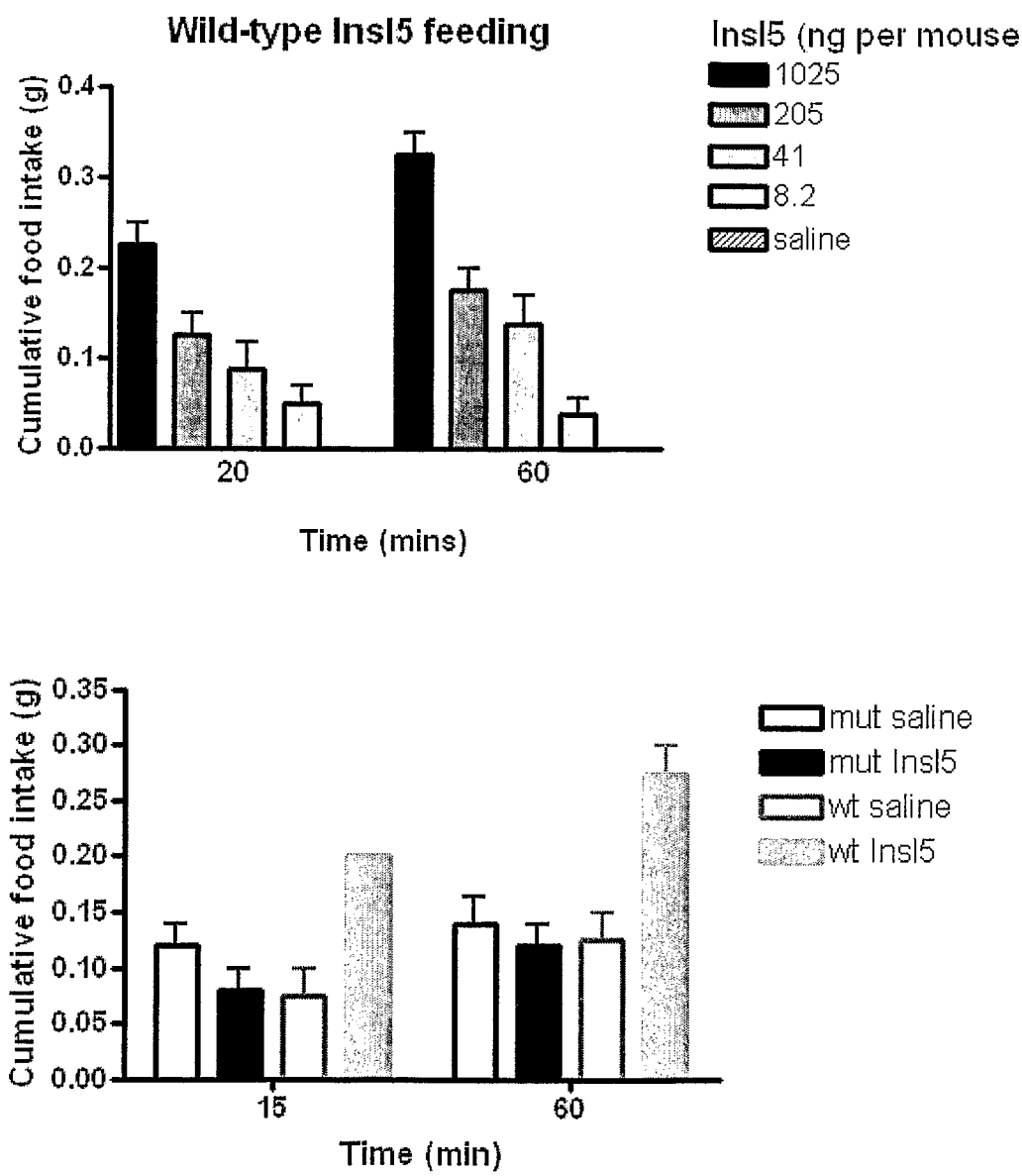
FIG. 9 illustrates that Insl5 induces, in a dose-dependant manner, an increase of food intake in wild-type mice (upper panel), while having no effect on feeding behaviour in GPR100 deficient mice (lower panel)

To test the hypothesis that Insl5 is an orexigenic hormone directly, it was administered intraperitoneally to wt and GPR100−/− mice. Insl5 induces, dose dependently, an increase of food intake in wt animals (FIG. 9, upper panel). In GPR100−/− mice Insl5 has no effect on feeding behaviour (FIG. 9, lower panel). This demonstrates that Insl5 has an orexigenic effect. Moreover, this effect is mediated through GPR100.

Example 4

Colon Motility is Altered in Gpr100−/− Mice

Figure 10:
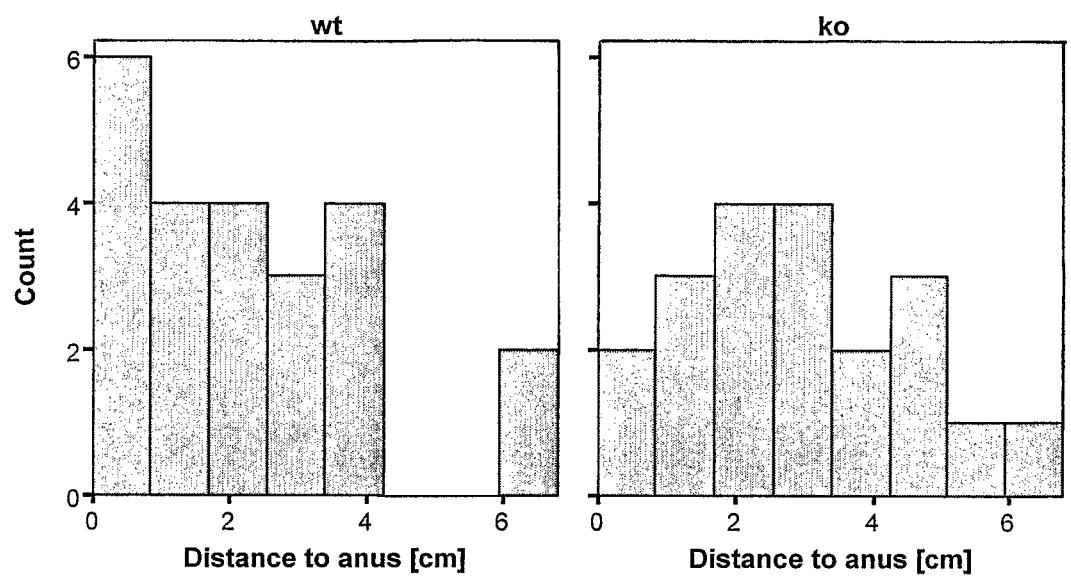
FIG. 10 illustrates the distribution of pellets in the colon of wild-type and GPR100-deficient mice.

Published and internal expression data suggest expression of both, Insl5 and GPR100 in the colon. This could indicate that this ligand receptor system is involved in the regulation of colon motility. Up to 90% of the volume entering the colon from the ileum is absorbed on its travel through the colon. The remainder is compacted in pellets which move slower the closer they get to the anus as a consequence of the decreasing volume. Mature pellets ready for defecation are stored in the rectum. Defecation is triggered by different mechanisms, one of which is the gastroanal reflex. Gastric distention due to consumption of a large meal triggers defecation. To explore the potential involvement of GPR100 in these mechanisms ad libitum fed animals were killed and the position of pellets was measured as distance to the anus in explanted colon. The frequency distribution over the distance to anus in wt animals is in conjunction with the decreasing velocity in more distal parts of the colon. Consequently, most pellets were observed in the last 9 mm of the colon (FIG. 10). The distribution in the GPR100−/− animals is similar in the more proximal colon segments, but the content of pellets in the two most distal segments is decreasing which indicates that the pellets are released instead of being stored for some time.

These findings are not the only indication that GPR100 and Insl5 are involved in the regulation of gastrointestinal motility. The release of gastrointestinal hormones is often triggered by different mechanisms. The early phase is often mediated by the nervous system whereas later phases are often triggered by direct contact of the nutrients with the intestinal wall. The observed phase shift in Insl5 secretion in ad libitum fed GPR100−/− animals indicates that this triggering by direct contact of the intestinal wall with the nutrient bolus occurs later thus leading to a delayed suppression of Insl5 secretion (FIG. 3). A similar phase delay is observed after re-feeding fasted animals (FIG. 2). Furthermore, in both the ad libitum and the refeeding experiment there is some indication that GLP1 and Ghrelin are phase-shifted as well.

Therapeutic Utility

The conclusion from the above findings is that INSL5 is an orexigenic enteroendocrine hormone. Its secretion is regulated by the feeding condition. Specifically, food consumption suppresses Insl5 secretion whereas fasting induces. Given its main expression in the colon the early (15 min) suppression of the high plasma levels in fasted animals is probably due to neuronal or endocrine signals. The low levels in the late phase might be mediated by direct effects of the nutrients in the colon.

The data indicates that the colonic motility is inhibited by Insl5 in the distal parts of the rectum which might lead to premature defecation. In contrast to the delay of defecation, Insl5 promotes the motility on the GI tract as a whole.

Insl5 antibodies are also useful in the treatment of obesity and the associated features of the metabolic syndrome. This approach is likely to be even more powerful if combined with Ghrelin antibodies. Furthermore, Insl5 itself is useful to treat anorexia nervosa, bulimia, cachexia, or diarrhoea-IBS.

The invention claimed is:

1. A method for treating a disease characterized by reduced appetite, comprising administering Insl5 to a subject suffering from the disease.

2. The method according to claim 1, wherein the disease is anorexia nervosa, bulimia, cachexia or wasting disease.

3. The method according to claim 1, wherein the method further comprises administering Ghrelin, or a derivative or fragment thereof that retains the ability to bind hGHSR1a, to the subject.

4. A method for altering food intake and weight of a subject, comprising administering Insl5, thereby altering the food intake and weight of the subject.

* * * * *

UNITED STATES PATENT AND TRADEMARK OFFICE
CERTIFICATE OF CORRECTION

PATENT NO. : 8,642,539 B2  Page 1 of 1
APPLICATION NO. : 12/675724
DATED : February 4, 2014
INVENTOR(S) : Grosse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 576 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 135
<212> TYPE: PRT
<213> ORGANISM: Homo sapiens
<220> FEATURE:
<221> NAME/KEY: VARIANT
<222> LOCATION: (115)..(115)
<223> OTHER INFORMATION: Residue can be pyroglutamate, glutamic acid,
      glutamine or a substance that yields glutamic acid upon acid
      hydrolysis

<400> SEQUENCE: 1

Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
        35                  40                  45

His Leu Glu Gly Ile Pro Gln Ala Gln Gln Ala Glu Thr Gly Asn Ser
    50                  55                  60

Phe Gln Leu Pro His Lys Arg Glu Phe Ser Glu Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110
```

-continued

```
Ser Arg Xaa Asp Leu Gln Thr Leu Cys Cys Thr Asp Gly Cys Ser Met
        115                 120                 125

Thr Asp Leu Ser Ala Leu Cys
    130                 135

<210> SEQ ID NO 2
<211> LENGTH: 21
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Residue can be pyroglutamate, glutamic acid,
      glutamine or a substance that yields glutamic acid upon acid
      hydrolysis

<400> SEQUENCE: 2

Xaa Asp Leu Gln Thr Leu Cys Cys Thr Asp Gly Cys Ser Met Thr Asp
1               5                   10                  15

Leu Ser Ala Leu Cys
            20

<210> SEQ ID NO 3
<211> LENGTH: 24
<212> TYPE: PRT
<213> ORGANISM: Homo sapiens

<400> SEQUENCE: 3

Lys Glu Ser Val Arg Leu Cys Gly Leu Glu Tyr Ile Arg Thr Val Ile
1               5                   10                  15

Tyr Ile Cys Ala Ser Ser Arg Trp
            20
```